United States Patent [19]

Chang

[11] Patent Number: 5,066,463
[45] Date of Patent: Nov. 19, 1991

[54] MULTIPLE-PURPOSE FECAL EXAMINATION APPARATUS

[76] Inventor: Maw-Guay Chang, P.O. Box 55-1670, Taipei (10477), Taiwan

[21] Appl. No.: 591,361

[22] Filed: Oct. 1, 1990

[51] Int. Cl.⁵ ............................................. G01N 21/00
[52] U.S. Cl. ..................................... 422/56; 422/58; 422/61; 422/101; 436/66; 436/169
[58] Field of Search ..................................... 422/56–61, 422/101, 102, 104; 436/66, 169, 904

[56] References Cited

U.S. PATENT DOCUMENTS

| | | | |
|---|---|---|---|
| 4,365,970 | 12/1982 | Lawrence et al. | 436/66 |
| 4,645,743 | 2/1987 | Baker et al. | 422/56 |
| 4,729,875 | 3/1988 | Chandler | 422/59 |
| 4,849,173 | 7/1989 | Chang | 422/56 |
| 4,994,238 | 2/1991 | Daffirn et al. | 422/56 |

Primary Examiner—Robert J. Hill, Jr.
Assistant Examiner—Laura E. Collins

[57] ABSTRACT

A fecal examination apparatus includes: an extension tube laterally protruding from an upper hollow portion of a housing so that a test reagent may be dripped into the extension tube to be in contact with a fecal sample in the tube for performing an occult blood test of liquid identification, and a platform formed on the upper hollow portion of the housing having two windows communicated with the hollow portion of the housing respectively overlaid with two filter papers respectively impregnated with reagents of high-sensitivity and low-sensitivity so that an occult blood test both for high sensitivity and low sensitivity can also be conducted on the two filter papers on the platform, thereby providing an instrument for examining fecal sample with multiple choices and purposes.

3 Claims, 4 Drawing Sheets

MULTIPLE-PURPOSE FECAL EXAMINATION APPARATUS

BACKGROUND OF THE INVENTION

U.S. Pat. No. 4,849,173 also invented the same applicant of this application includes a handle member having an elongate stirrer inserted in a housing. Whenever conducting an occult blood test by using such a conventional examination unit, a whole unit including an upper portion 20 and a lower base portion 21 of the housing 2 should be used simultaneously, wherein a medical saline solution is fed into the upper chamber 20a for dissolving the fecal sample which is stirred by the stirrer, and then the fecal solution is drained into the lower chamber 20c to be absorbed on the filter 6 for occult blood test through slot 200. The remaining fecal solution will be discharged through the bottom tube 211, into a test tube for additional test such as for the inspection of parasites. However, in some circumstances, if only the occult blood test is necessary, the complete unit must be used to increase waste disposal problem since a further test tube is still required to receive the fecal solution filtered by filter 6, causing inconvenience for a busy laboratorian's work.

The present inventor has found such phenomena and invented the present multiple-purpose fecal examination apparatus.

SUMMARY OF THE INVENTION

The object of the present invention is to provide a fecal examination apparatus including an extension tube laterally protruding from an upper hollow portion of a housing so that a test reagent may be dripped into the extension tube to be in contact with a fecal sample in the tube for performing an occult blood test of liquid identification, and a platform formed on the upper hollow portion of the housing having two windows communicated with the hollow portion of the housing respectively overlaid with two filter papers respectively impregnated with reagents of high-sensitivity and low-sensitivity so that an occult blood test both for high sensitivity and low sensitivity can also be conducted on the two filter papers on the platform, thereby providing an instrument for examining fecal sample with multiple choices and purposes.

DETAILED DESCRIPTION

Figure 1:
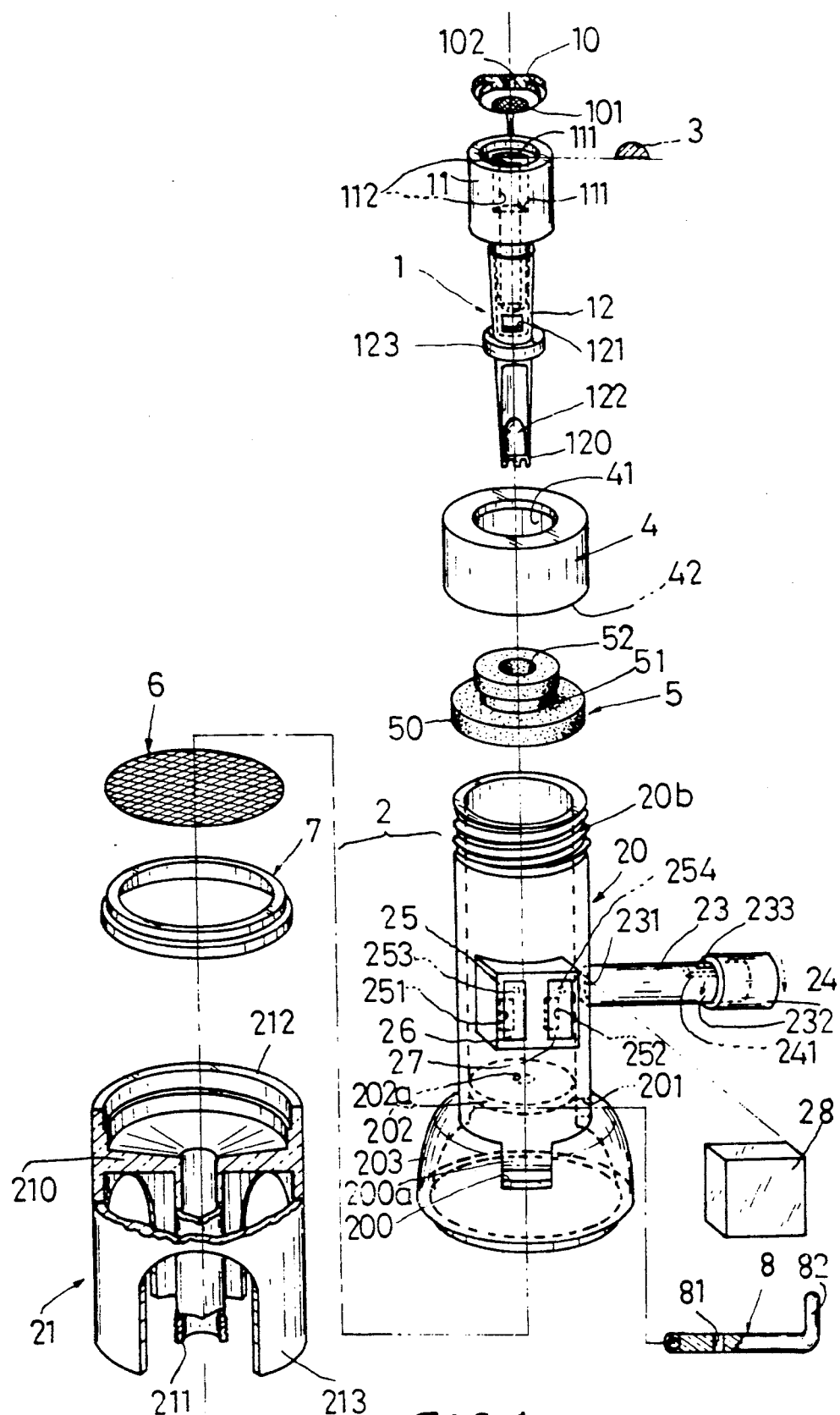
FIG. 1 is an illustration showing all elements in construction of the present invention.

As shown in FIG. 1-4, the present invention comprises: a handle means 1 and a housing 2.

The handle means 1 includes: a tubular handle portion 11 having an uppermost cover 10 removably formed on a top end of the handle portion 11, a hollow stem 12 connected to and positioned under the tubular handle 11 having s stirring rake member 120 formed on a lower portion of the stem 12.

The hollow stem 12 is inserted in a central hole 52 of a soft packing member 5 having a retainer ring 123 formed on the stem 12 to prevent a withdrawal of the stem 12 from the packing member 5 once picking up a fecal sample. The hollow stem 12 is formed with venting hole or holes 121 fluidically communicated with a venting hole 112 formed in handle portion 11 and a top venting hole 102 formed in cover 10 for directing air into chamber 20a. A shallow recess 122 is formed in a lower portion of stem 12 approximate to the rake member 120 for collecting aqueous fecal sample thereon. A cavity 111 is formed in the handle portion 11 to be filled with standard blood for quality control use. A membrane 3 is provided to cover the cavity 111. The area of cavity 111 may occupy two third of a cross sectional area of the tubular handle portion 11, whereas the area of venting hole 112 occupies one third of the cross sectional area of the handle portion 11. A standard test paper 101 for contrast use is adhered on an inside surface of the cover 10.

The hollow stem 12 once inserted into the packing member 5 may be retained on the member 5 since a diameter of the tubular handle portion 11 is larger than that of the stem 12. The packing member 5 may be made of elastomers of rubber or plastic materials for sealing the fecal solution in the housing 2.

The housing 2 for encasing and supporting the handle means 1 includes: an upper hollow portion 20 and a lower base portion positioned under the upper hollow portion 20 generally separated by a first partition plate 210.

A cap 4 includes a central cap hole 41 sealably engaged by a neck portion 51 of the packing member 5, a female-threaded portion 42 engageable with a male-threaded portion 20b formed on an upper edge portion of the upper hollow portion 20. A lower extension 50 of the packing member 5 is packed by the cap 4 and a top end portion of the hollow portion 20.

Figures 2, 3:
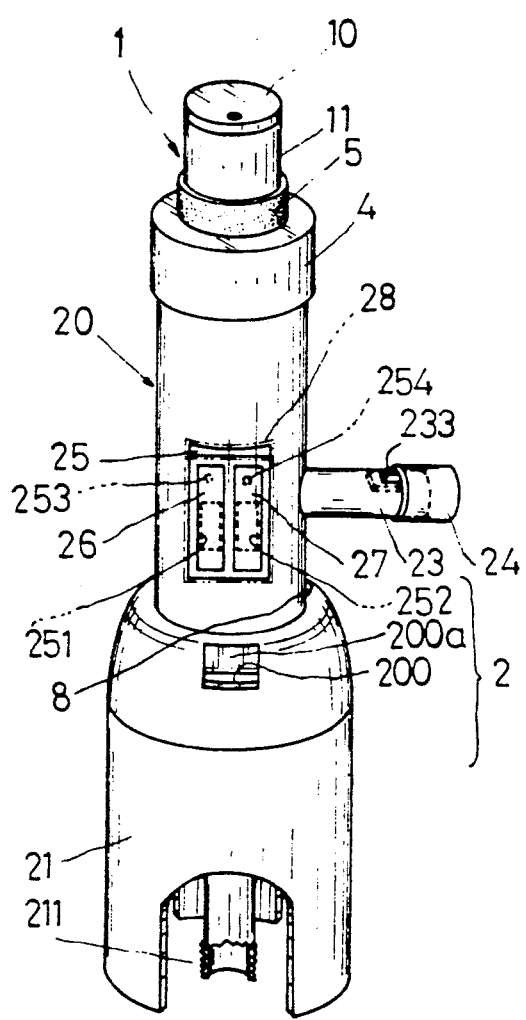
FIG. 2 is a sectional drawing of the present invention as assembled.
FIG. 3 is a perspective view of the present invention.
Figure 4:
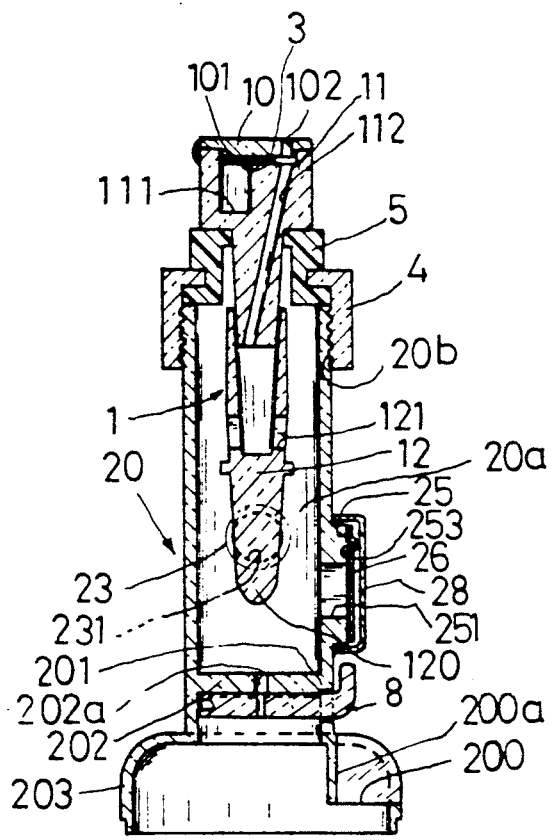
FIG. 4 is a sectional drawing of the present invention when removing a lower base portion of a housing.

The upper hollow portion 20 includes a lower skirt portion 203 engageable with an upper extension 212 of the lower base portion 21 for coupling the upper portion 20 with the lower portion 21 as packed by a retainer 7 having a filter means 6 bounded on the retainer 7. A second partition plate 202 is formed in a central portion of the housing 2 to define an upper chamber 20a between the cap 4 and the second plate 202, and to define a lower chamber 20c between the second plate 202 and the first plate 210 as shown in FIG. 2.

The second partition plate 202 is formed with a drain hole 222a in its central portion, having a cylindrical rod valve 8 pivotally mounted in the hollow portion 20 drilled with a central rod hole 81 operatively communicated with the drain hole 202a and a valve handle 82 protruding outwardly through a side hole 201 formed in the upper portion 20 for rotating the rod valve 8 for matching the rod hole 81 with the drain hole 202a or not.

The lower skirt portion 203 includes a slot 200 having partition wall or walls 200a shielding the lower chamber 20c to allow quantitative fecal solution penetrating outwardly through the slot 200 for test purpose.

The lower base portion 21 includes a bottom tube 211 protruding downwardly from the plate 210 connected to a test tube (not shown) for further test purpose. If not connected with further test tube, the supporting legs 213 may support the housing 2 and the handle means 1 on a table.

An extension tube 23 is protruded laterally from a side portion of the upper hollow portion 20 above the second partition plate 202, having a cross sectional area of the tube 23 smaller than a diameter of the hollow portion 20.

The extension tube 23 includes an inner tube port 231 communicated with the upper chamber 20a, a dripping hole 233 formed on an outer portion of the tube 23, and a rotating knob 24 rotatably mounted on an outer end portion of the tube 23 having a shielding lug 241 protruding inwardly for rotatably closing the dripping hole 233.

The upper hollow portion 20 is also formed with a platform 25 on a side of the extension tube 23, which platform 25 includes a left window 251, and a right window 252 respectively communicated with the upper chamber 20a, two protrusion points 253, 254 respectively formed on the platform 25 above the two window 251, 252, two filter papers 26, 27 overlaid on the two windows 251, 252 impregnated with test reagent of high sensitivity and low sensitivity, and a protective cover 28 shielding the filter papers 26, 27 and the platform 25.

Figure 5:
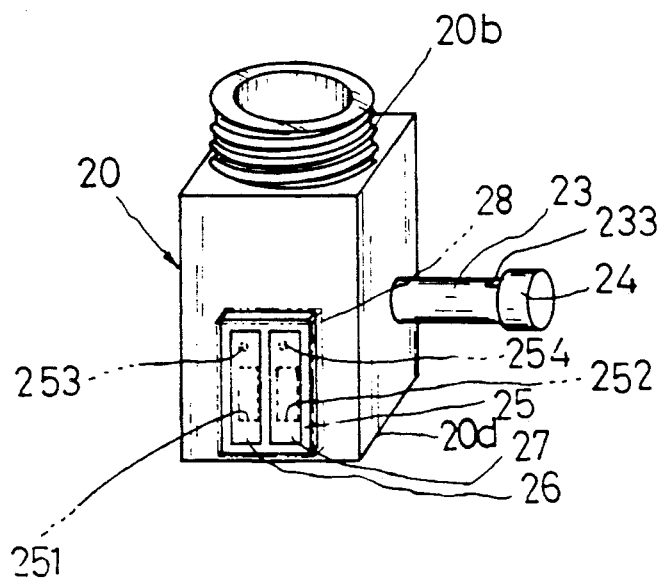
FIG. 5 shows another preferred embodiment of the present invention having an upper hollow portion of the housing.

The present invention may be made as cylindrical shape or made as a rectangular column as shown in FIG. 5 of which the bottom portion 20d may be closed, serving as an unit merely for occult blood test. Of course, the device as shown in FIG. 5 may be modified to be the system as shown in FIGS. 1-3 to further include a base portion 21 for supporting the upper portion 20.

Figure 6:
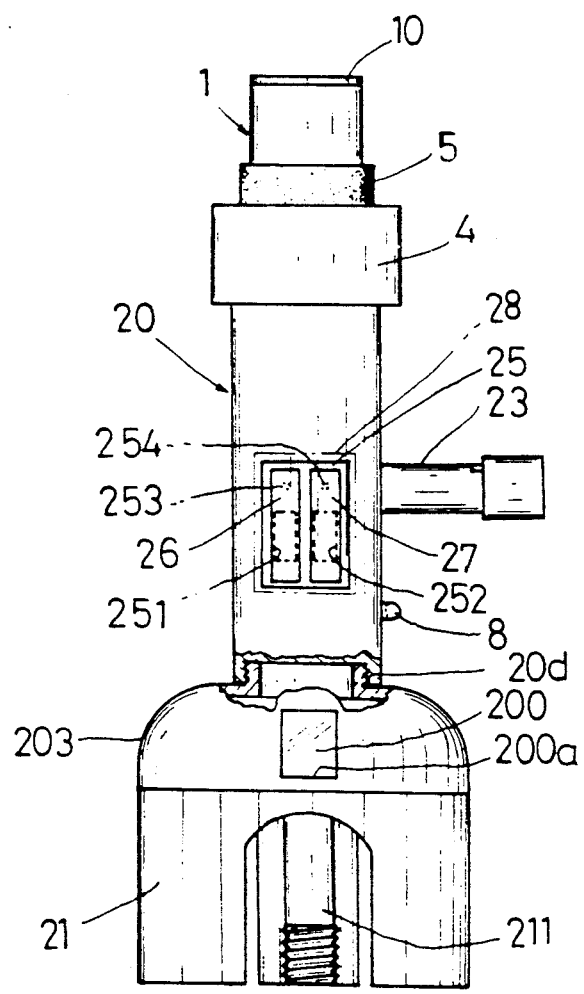
FIG. 6 shows still another preferred embodiment of the present invention.

The preferred embodiment as shown in FIG. 6 disclose a threaded bottom portion 20d of the upper hollow portion 20 for engageably connecting the lower skirt portion 203 and the lower base portion 21.

The present invention may be modified without departing from the scope and spirit of this invention by those skilled in the art.

In using the present invention, the following examples of procedures may be adopted:

EXAMPLE A

For performing quality control test on the uppermost cover 10: 1. The standard test paper 101 in the cover 10 is dripped with reagent and bovine hemoglobin. If the test paper is changed from red to blue color, it denotes that the paper and reagent quality is effective for test use. 2. Opening cover 10 and membrane 3, the reagent and bovine hemoglobin may also be added into cavity 111 for quality control test. 3. By dripping a drop of reagent and hemoglobin on the filter papers 26, 27 at each protrusion point 253, 254, a positive reaction proves that the paper and reagent is effective for test purpose.

EXAMPLE B

An occult blood test is conducted in the upper hollow portion 20 and extension tube 23 as follows: 1. The rake member 120 is used to pick up a fecal sample about 0.5-1 gram which is put into the hollow portion 20 and the cap 4 is closed. The inner port 231 of the extension tube 23 is coated or spread with the fecal sample. A high-sensitivity reagent such as O-toluidine or Tetramethyl benzidine, and hydrogen peroxide is injected into the upper chamber 20a through the soft packing member 5 by a dispenser. If a blue color occurs, it indicates a positive occult blood having hemorrhage present in fecal sample. 2. If the above-mentioned high-sensitivity test has no blue reaction, there is no need to proceed a low-sensitivity test. 3. However, if the high-sensitivity test reveals blue positive reaction, a false test result may occur such as being interferred by accidentally eating blood of the other animals, thereby requiring a further test of low sensitivity. 4. A test reagent of low sensitivity such as Guaiac resin or Lignumvitae resin and $H_2O_2$ is dripped through port 233 into the extension tube 23 for semi-quantitative reaction. If a blue color occurs, it indicates a positive reaction showing hemorrhage present in fecal sample.

EXAMPLE C

By conducting test on the platform 25 of the upper hollow portion 20, the following procedures are taken: 1. The fecal sample is charged into the upper chamber 20a and spread on the windows 251, 252. 2. The left filter paper 26 is pre-impregnated with high-sensitivity test reagent, whereas the right filter paper 27 is pre-soaked with low-sensitivity reagent. The fecal sample will be penetrated into the filter papers. 3. Removing the protective cap 28 and dripping several drops of hydrogen peroxide on the papers, a blue color occurs to indicate a positive reaction of occult blood test.

EXAMPLE D

Both the upper hollow portion 20 and the lower base portion 21 of the housing 2 of this invention are used for conducting the test and analysis as follows: 1. A medical saline water is injected into the upper chamber 20a through the packing member 5 and is stirred with the fecal sample added into the chamber 20a. A volumetric ratio of saline water to fecal sample ranges from 1:4 to 1:5. 2. The bottom tube 211 of the lower base portion 21 is connected to a centrifugal test tube. The valve 8 is opened to drain fecal solution through holes 202a, 81 to be filtered through the filter 6 and discharged into the test tube for further laboratory test such as for inspecting parasites by using centrifungal concentration method or for examining other pathologic properties or matters such as red blood cells or white blood cells. 3. During the drainage of fecal solution, a test paper may also be incorporated into the lower chamber 20c to absorb the fecal solution from the filter 6. By dripping reagents into the test paper, an occult blood test may thus be done. (Note: The extension tube 23 or platform 25 formed on the upper portion 20 may not be used at this time or may serve for other auxiliary tests).

The present invention is further provided with the laterally protruding extension tube 23 and platform 25 for multiple choices in conducting occult blood tests. Furthermore, a high-sensitivity test and a low-sensitivity test may be simultaneously or selectively performed by this invention.

The upper portion 20 may be separated from the lower portion 21 of the invention for an independent test purpose, and may also be combined with the lower base portion 21 for more complete test or analysis.

I claim:

1. A multiple-purpose fecal examination apparatus comprising:
a handle means including a tubular portion having a hollow stem formed on a lower portion of the tubular handle portion and a rake member formed on a bottom portion of said stem, a shallow recess portion formed in a lower portion of said stem approximate to said rake member;

a housing including an upper hollow portion for encasing and supporting said handle means and a lower base portion having a bottom tube adapted for connecting a test tube, said handle means having said hollow stem inserted in a soft packing member sealably mounted on an upper portion of said housing, said lower base portion having a first partition plate separating said upper hollow portion and said lower base portion and having a filter retained on said first partition plate and a slot formed in said upper hollow portion adjacent to said filter for inserting a test paper through said slot for an occult blood test, said upper hollow portion having a second partition plate having a central drain hole formed therein and a valve means formed under said second partition plate for operatively opening said drain hole for draining a fecal solution downwardly into a test tube connected to said bottom tube of said lower base portion for inspecting parasites, said second partition plate defining an upper chamber and a lower chamber in said upper hollow portion;

an extension tube laterally protruding from said upper hollow portion above said second partition plate communticated with said upper champer, having a dripping hole formed in an outer portion of said extension tube rotatably closed by a rotating knob rotatably mounted on an outer end portion of said extension tube; and a platform formed on said upper hollow portion on a side of said extension tube having two windows formed in said platform communicated with said upper chamber, and two filter papers pre-soaked or pre-impregnated with test reagents thereon overlain on said two windows, and a protective cap shielding said filter papers and said platform;

whereby upon a charge of fecal sample into said upper chamber to spread the fecal sample on an inner port of said extension tube or on the two windows of said platform for penetrating fecal samples onto the filter papers, the test reagents may be added through the dripping hole into said extension tube or may be applied on said filter papers for conducting occult blood test of the fecal sample.

2. A fecal examination apparatus according to claim 1, wherein said tubular handle portion includes an uppermost cover and a cavity formed in said handle portion for filling test reagent for quality control use, and a venting hole formed in said cap, said handle portion fluidically communicated with a venting hole formed in said stem, said hollow stem having a limiting extension formed thereon for preventing its withdrawal from said packing member capped on said upper hollow portion of said housing.

3. A fecal examination apparatus according to claim 1, wherein said platform is formed with two protrusion points respectively positioned above said two windows for dripping test reagents thereon for quality control use.

* * * * *